(12) United States Patent
Stuber et al.

(10) Patent No.: US 10,455,760 B2
(45) Date of Patent: Oct. 29, 2019

(54) SYSTEMS, METHODS, AND APPARATUS FOR CROP INPUT VARIETY SELECTION

(71) Applicant: Precision Planting LLC, Tremont, IL (US)

(72) Inventors: Luke Stuber, Tremont, IL (US); Justin Vollmer, Morton, IL (US); Timothy Schaefer, Tremont, IL (US)

(73) Assignee: Precision Planting LLC, Tremont, IL (US)

( * ) Notice: Subject to any disclaimer, the term of this patent is extended or adjusted under 35 U.S.C. 154(b) by 192 days.

(21) Appl. No.: 15/825,929

(22) Filed: Nov. 29, 2017

(65) Prior Publication Data

US 2018/0148276 A1    May 31, 2018

Related U.S. Application Data

(60) Provisional application No. 62/428,217, filed on Nov. 30, 2016.

(51) Int. Cl.
| | |
|---|---|
| *A01C 7/10* | (2006.01) |
| *A01C 21/00* | (2006.01) |
| *A01C 14/00* | (2006.01) |
| *G01F 23/292* | (2006.01) |
| *G01N 15/02* | (2006.01) |
| *A01C 7/04* | (2006.01) |
| *G01F 23/26* | (2006.01) |
| *G01F 23/296* | (2006.01) |

(52) U.S. Cl.
CPC .............. *A01C 21/005* (2013.01); *A01C 7/10* (2013.01); *A01C 14/00* (2013.01); *G01F 23/292* (2013.01); *G01N 15/02* (2013.01); *G01N 15/0205* (2013.01); *A01C 7/046* (2013.01); *G01F 23/26* (2013.01); *G01F 23/2962* (2013.01)

(58) Field of Classification Search
CPC ........... A01C 7/10; A01C 7/046; A01C 14/00; A01C 21/005; A01C 23/26; A01C 23/292; A01C 23/2962; A01C 15/02; A01C 15/0205
See application file for complete search history.

(56) References Cited

U.S. PATENT DOCUMENTS

| | | | |
|---|---|---|---|
| 8,942,894 B2 * | 1/2015 | Garner | A01C 7/10 701/50 |
| 8,948,980 B2 * | 2/2015 | Garner | A01C 7/08 111/185 |
| 9,179,594 B2 * | 11/2015 | Graham | A01C 7/04 |
| 9,615,504 B2 * | 4/2017 | Sauder | A01C 21/005 |
| 9,936,625 B2 * | 4/2018 | Wendte | A01C 21/005 |

(Continued)

*Primary Examiner* — Patrick O Neill
(74) *Attorney, Agent, or Firm* — Jaffery Watson Mendonsa & Hamilton LLP

(57) ABSTRACT

Described herein are systems, methods, and apparatus for agricultural planting including selecting and varying agricultural input types during an in-field operation. In one embodiment, a method of calculating a volume of a seed during planting comprises adding a known volume of seed to a seed pool that has a fill level sensor. The method further includes dispensing seeds from the seed pool and as the seeds are dispensed, counting the number of seeds with a seed sensor. The method further includes stopping counting when the fill level sensor indicates no seeds present and calculating seed volume by dividing the known volume by the number of seeds counted.

20 Claims, 13 Drawing Sheets

(56) References Cited

U.S. PATENT DOCUMENTS

| | | | | |
|---|---|---|---|---|
| 9,974,230 B2* | 5/2018 | Sauder | ................... | A01C 7/046 |
| 10,159,176 B2* | 12/2018 | Baitinger | ............. | A01C 21/005 |
| 2018/0035603 A1* | 2/2018 | Kremmer | ............. | A01C 21/005 |
| 2018/0124998 A1* | 5/2018 | Swanson | .............. | A01C 21/005 |

\* cited by examiner

SYSTEMS, METHODS, AND APPARATUS FOR CROP INPUT VARIETY SELECTION

RELATED APPLICATIONS

This application claims the benefit of U.S. Provisional Application No. 62/428,217, filed on Nov. 30, 2016, the entire contents of which are hereby incorporated by reference.

TECHNICAL FIELD

Embodiments of the present disclosure relate to systems, methods, and apparatus for agricultural planting including effectively selecting and varying agricultural input types during an in-field operation.

BACKGROUND

In recent years, the ability to control crop input applications on a site-specific basis (known as "precision farming") has increased interest in varying input types throughout a field. In particular, advances in seed genetics and agronomic research have increased the need for solutions enabling the variation of seed types in the field during a planting operation. Some proposed solutions involve shifting between input types fed to the metering units, which may result in blending of input types at the metering units and thus blended input regions in the field.

BRIEF DESCRIPTION OF THE DRAWINGS

The present disclosure is illustrated by way of example, and not by way of limitation, in the figures of the accompanying drawings and in which.

BRIEF SUMMARY

In one embodiment, a process for determining seed volume of seeds used during planting is described herein.

DETAILED DESCRIPTION

There is a need in the art for systems, methods and apparatus for effectively selecting and varying agricultural input types during an in-field operation to quickly transition between input types to limit blending between seed types. In one embodiment, a method of calculating a volume of a seed during planting comprises adding a known volume of seed to a seed pool that has a fill level sensor. The method further includes dispensing seeds from the seed pool and as the seeds are dispensed, counting the number of seeds with a seed sensor. The method further includes stopping counting when the fill level sensor indicates no seeds present and calculating seed volume by dividing the known volume by the number of seeds counted.

Figure 1:
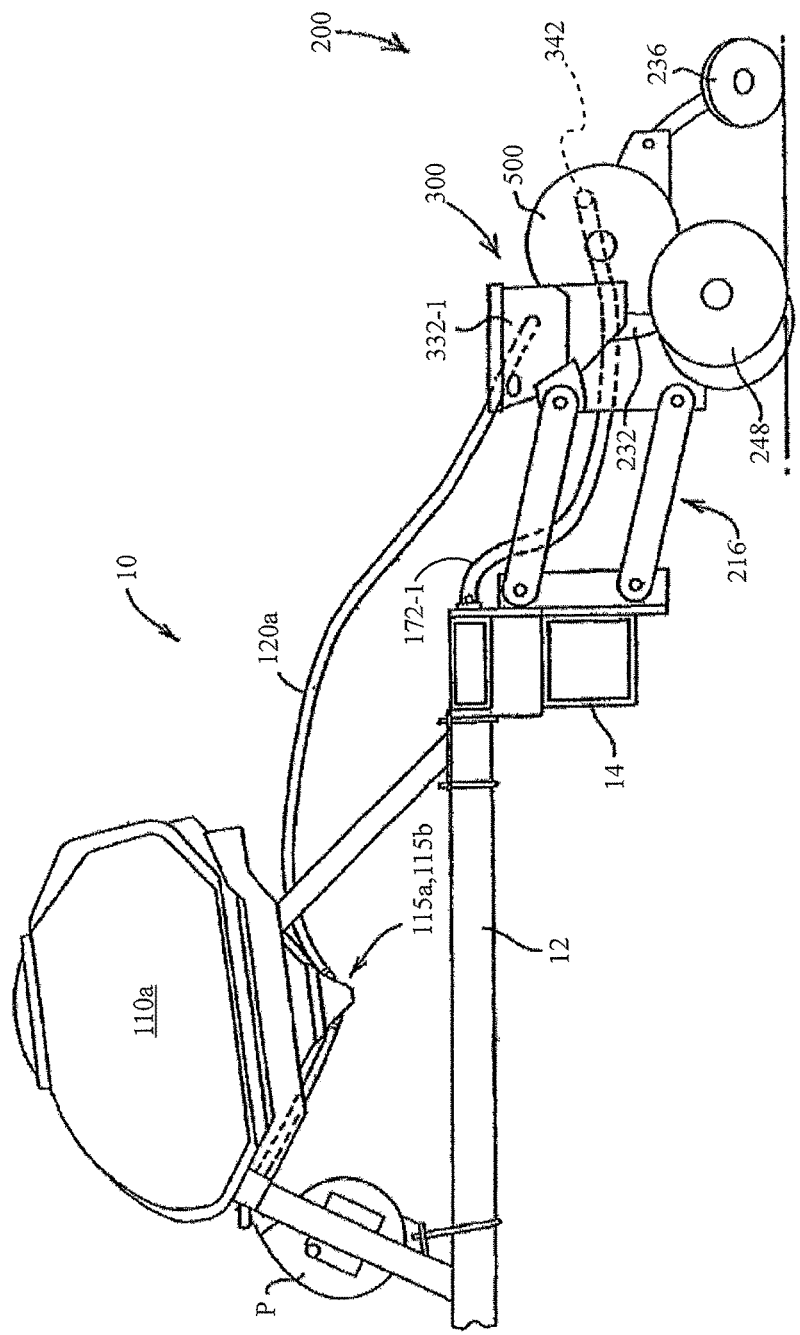
FIG. 1 is a side elevation view of an embodiment of a row crop planter.

Referring now to the drawings, wherein like reference numerals designate identical or corresponding parts throughout the several views, FIG. 1 illustrates a planter 10 having a frame 12 including a transversely extending toolbar 14. A plurality of row units 200 are mounted to the toolbar 14 in transversely spaced relation. A plurality of bulk hoppers 110 are preferably supported by the frame 12 and in seed and pneumatic communication with the row units 200.

Figure 2:
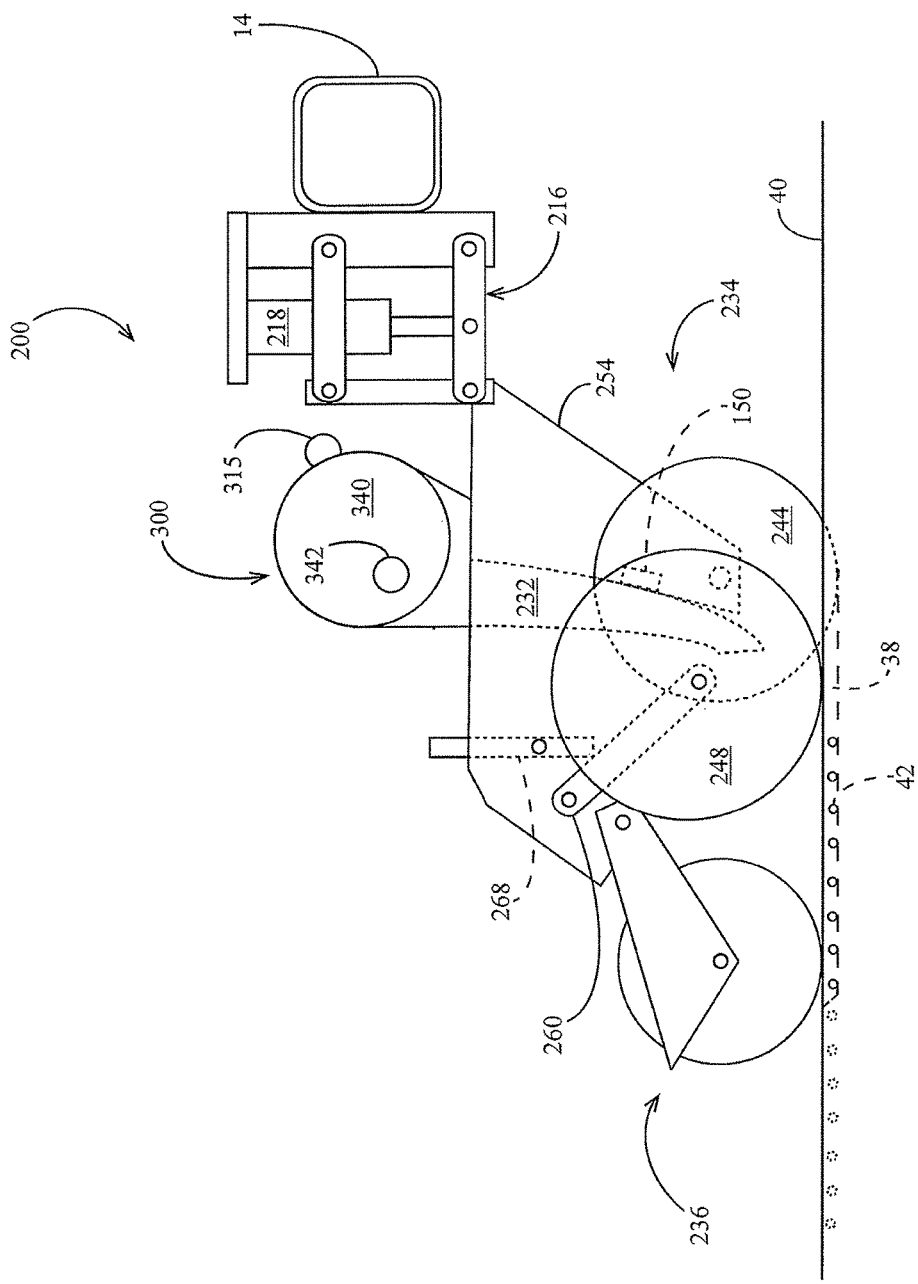
FIG. 2 is a side elevation view of an embodiment of a planter row unit.

Turning to FIG. 2, an embodiment is illustrated in which the row unit 200 is a planter row unit. The row unit 200 is preferably pivotally connected to the toolbar 14 by a parallel linkage 216. An actuator 218 is preferably disposed to apply lift and/or downforce on the row unit 200. A solenoid valve (not shown) is preferably in fluid communication with the actuator 218 for modifying the lift and/or downforce applied by the actuator. An opening system 234 preferably includes two opening discs 244 rollingly mounted to a downwardly-extending shank 254 and disposed to open a v-shaped trench 38 in the soil 40. A pair of gauge wheels 248 is pivotally supported by a pair of corresponding gauge wheel arms 260; the height of the gauge wheels 248 relative to the opener discs 244 sets the depth of the trench 38. A depth adjustment rocker 268 limits the upward travel of the gauge wheel arms 260 and thus the upward travel of the gauge wheels 248. A downforce sensor (not shown) is preferably configured to generate a signal related to the amount of force imposed by the gauge wheels 248 on the soil 40; in some embodiments the downforce sensor comprises an instrumented pin about which the rocker 268 is pivotally coupled to the row unit 200, such as those instrumented pins disclosed in Applicant's U.S. Patent Publication No. US2010/10180695, the disclosure of which is hereby incorporated herein by reference.

Continuing to refer to FIG. 2, a seed meter 300 such as that disclosed in Applicant's International Patent Application No. PCT/US2012/030192 ("the '192 application"), the disclosure of which is hereby incorporated herein by reference, is preferably mounted to the row unit 200 and disposed to deposit seeds 42 into the trench 38, e.g., through a seed tube 232 disposed to guide the seeds toward the trench. In other embodiments, the seed tube 232 is replaced with a seed conveyor such as that disclosed in Applicant's International Patent Application No. PCTIUS2012/057327 ("the '327 application") or Applicant's U.S. Provisional Patent Application No. 621192,309, both of which are incorporated herein by reference. In alternative embodiments, a plurality of seed meters 300 may be mounted to the row unit 200 and disposed to deposit seeds 42 into the same trench 38, e.g., through the same seed tube 232 or seed conveyor.

Figure 5:
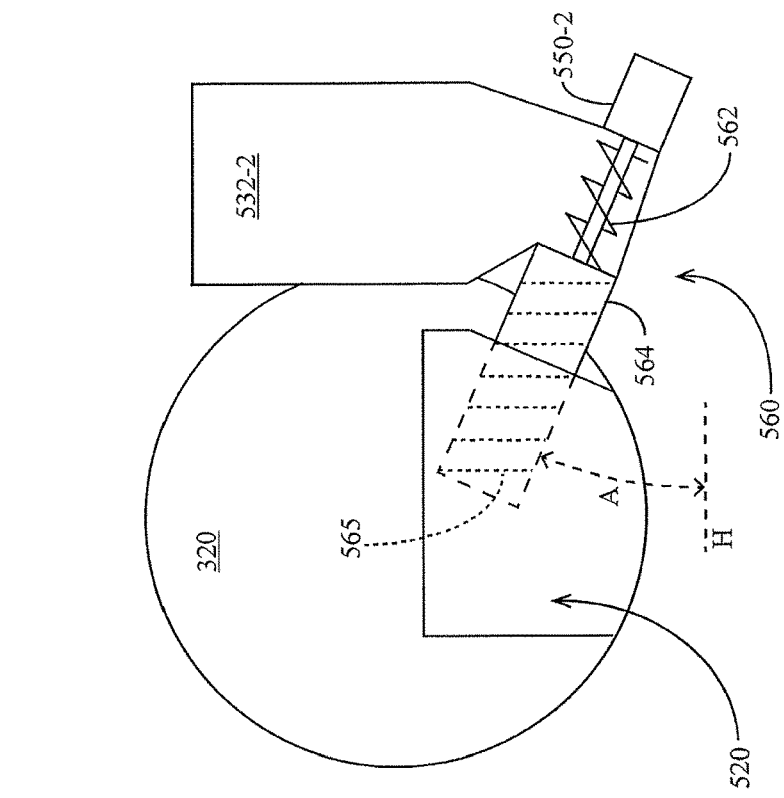
FIG. 5 is a side elevation view the embodiment of FIG. 4.
Figure 4:
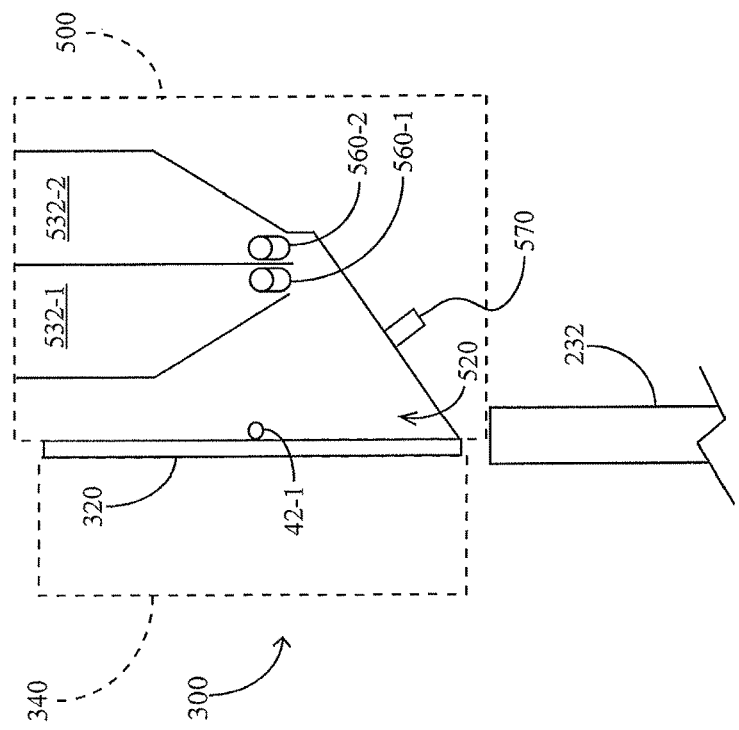
FIG. 4 is a front elevation view of an embodiment to selectively supply seed to a seed meter from different auxiliary hoppers.

Referring to FIGS. 2, 4 and 5, the seed meter 300 preferably includes a seed side housing 500 having a first auxiliary hopper 532-1 for storing seeds 42 to be deposited by the seed meter and a second auxiliary hopper 532-2 for storing seeds 42 to be deposited by the seed meter. The seed meter 300 preferably includes a vacuum side housing 340 including a vacuum port 342 for pulling a vacuum within the vacuum side housing 340. The seed meter 300 preferably includes a seed disc 320 including a plurality of seed apertures (not shown); the seed disc 320 preferably separates interior volumes of the vacuum side housing 340 and the seed side housing 500. In operation, seeds 42 communicated from the auxiliary hoppers 532 into a seed pool 520 of the seed side housing 500 are captured on the seed apertures due to the vacuum in the vacuum side housing 340 and then released into the seed tube 232 (or seed conveyor). The seed meter 300 is preferably powered by individual electric drives 315. Each drive 315 is preferably configured to drive the seed disc 320 within the seed meter 300. Each electric drive preferably comprises an electric drive such as one of the embodiments disclosed in International Patent Application No. PCT/US2013/051971 and/or U.S. Pat. No. 7,617,785, the disclosures of both of which are hereby incorporated herein in their entirety by reference. In alternative embodiments, the drive 315 may comprise a hydraulic drive or other motor configured to drive the seed disc. In one embodiment, seed meter 300 can be sized to minimize the volume of seed pool 520 so that there are fewer seeds in seed pool 520 that have to be managed as a variety boundary is approached.

Referring to FIGS. 4 and 5, seed is preferably selectively supplied to the seed pool 520 from one of the auxiliary hoppers 532-1, 532-2 at a time by selective actuation of one or more seed transfer actuators 550 which drive seed tenders 560-1, 560-2. The seed tender 560 being actuated transfers seed from its associated auxiliary hopper 532 to the seed pool 520. In the embodiment shown in FIG. 5, each seed tender 560 comprises an auger 564 (e.g., a cylindrical auger having internal flights). Each seed tender 560 preferably additionally includes a preloading auger 562 which preferably loads seeds into the auger 564 and preferably agitates seeds at the bottom of the associated auxiliary hopper 532. An inlet end of the auger 564 is preferably disposed vertically lower than an outlet end of the auger such that seed does not flow through the auger by gravity and instead flows only upon selective actuation of the auger. For example, the auger (e.g., a sidewall of the auger, a rotational and/or central axis of the auger, a transport vector along which seeds are tendered by the auger) may be disposed at an angle A (e.g., between 0 and 90 degrees; between 10 and 80 degrees; between 20 and 70 degrees; between 30 and 60 degrees; between 40 and 50 degrees; between 0 and 10 degrees; between 10 and 20 degrees; between 20 and 30 degrees; between 30 and 40 degrees; between 50 and 60 degrees; between 60 and 70 degrees; between 70 and 80 degrees; between 80 and 90 degrees; approximately 0, 5, 10, 15, 20, 25, 30, 35, 40, 45, 50, 55, 60, 65, 70, 75, 80, 85, or 90 degrees; 0, 5, 10, 15, 20, 25, 30, 35, 40, 45, 50, 55, 60, 65, 70, 75, 80, 85, or 90 degrees) relative to a horizontal plane H.

In operation, the auxiliary hoppers 532-1, 532-2 are filled with a first and second seed variety, respectively. The filling step may be completed by the central seed distribution system illustrated in FIG. 1 or manually by the operator. Seed is preferably not transferred from either of the auxiliary hoppers 532 to the seed pool 520 until one of the seed transfer actuators 550 drives an associated seed tender 560. Taking the seed tender 560-1 as an example, when the seed transfer actuator 550-1 operates the seed tender 560-1, seed is preferably transferred from the auxiliary hopper 532 to the seed pool 520 by operation of the seed transfer actuator. In the embodiment shown in FIG. 5, when the seed transfer actuator is operated (i.e., driven for rotation), rotation of the pre-loading auger 562 pushes seeds into an internal volume of the auger 564 and rotation of the auger 564 due to the motion of internal flights 565 extending along an inner surface of the auger 564.

Figure 7:
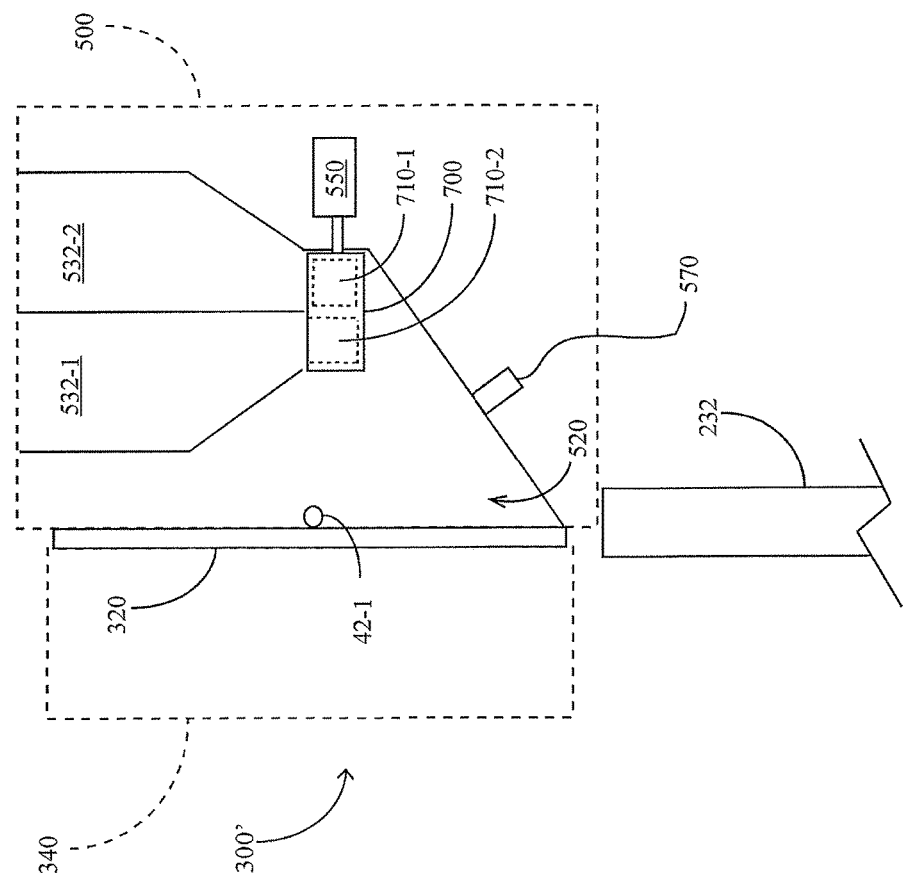
FIG. 7 is a side elevation view of another embodiment to selectively supply seed to a seed meter from different auxiliary hoppers.

In alternative embodiments, each seed tender 560 may be other structure configured to selectively transfer seed or permit seed transfer from an auxiliary hopper 532 to the seed pool 520. Some such embodiments include carousels, paddle wheels, dosing wheels, or gates. One such alternative embodiment is illustrated in FIG. 7, where the seed tender comprises a dosing element 700 having two dosing gates 710-1, 710-2 preferably disposed to receive seed from (e.g., vertically below a lower outlet of) the auxiliary hoppers 532-1, 532-2 respectively. In a first position (e.g., the orientation in which the dosing gate 710-1 is illustrated) the dosing gate prevents flow of seed from the associated auxiliary hopper by gravity into the seed pool 520 and preferably receives and stores a dose of seed from the associated auxiliary hopper in an interior volume of the dosing gate. In a second orientation (e.g., the orientation in which the dosing gate 710-2 is illustrated), seed is retained in the associated auxiliary hopper by contact with a sidewall of the dosing gate and is not allowed to enter the interior volume of the dosing gate. In a third position (not illustrated but preferably 180 degrees from the orientation in which the dosing gate 710-1 is illustrated), the dosing gate permits flow of seed from the interior volume of the dosing gate by gravity into the seed pool. The first and second dosing gates 710-1, 710-2 are preferably oriented relative to one another (e.g., at 90 degrees) such that the first dosing gate is in the first orientation when the second dosing gate is in the second orientation. In operation, the seed transfer actuator 550 preferably selectively rotates the dosing gates 710 between the first, second and third positions to selectively dose seed into the seed pool 520. For example, to meter a controlled amount of seed from auxiliary hopper 532-1, the first dosing gate 710-1 is preferably alternately rotated between the first and third orientations while the second dosing gate remains in the second position or moves through a range of positions in which seed does not enter the interior volume of the second dosing gate. In an alternative embodiment, the dosing gate may include an open position in which seed is permitted to flow from the associated hopper into the seed pool.

In some embodiments, a fill level sensor 570 (FIG. 4) is provided for sensing a fill level of the seed pool 520. The fill level sensor 570 may comprise an optical sensor provided in the seed pool 520 (e.g., paired with a light source which is only visible when the seed pool is not filled passed a threshold level). The fill level sensor 570 may alternatively comprise a range sensor (e.g., ultrasonic, ultrasound, capacitance) configured to measure a distance between the sensor and an upper surface of seeds accumulated in the seed pool 520. The fill level sensor 570 may alternatively comprise a capacitance sensor. In some embodiments, a first fill level sensor may be provided for determining whether the seed pool is filled to a first level and a second fill level sensor may be provided for determining whether the seed pool is filled to a second (e.g., higher or more full) level. A fill level sensor 570 simplifies the system by not having to count the number of seeds added to or dispensed from seed pool 520. The placement of fill level sensor 570 in the seed pool can be based on the volume of the seed pool at the location along with knowing the volume of each seed to translate into an approximate number of seeds. In some embodiments, there is no seed counter for counting the number of seeds that are supplied to seed pool 520. In one embodiment for corn seeds, fill level sensor 570 is disposed such that the level of seeds detected includes at least 150 seeds in the seed pool 520. When the seed pool 520 drops below fill level sensor 570, a signal is sent to the seed transfer actuator to open a flow path to a desired seed hopper (described below) to add more seeds to seed pool 520. The volume of the seed pool 520 can be minimized by making the space smaller, such as by including a baffle (not shown) to fill a portion of the volume.

The placement of fill level sensor 570 can assist in switching from one seed type to a second seed type such that the feeding from one auxiliary hopper is shut off as a boundary between seed variety regions is approached such that the number of seeds of a first type in seed pool 520 is minimized before crossing the boundary. Just before the boundary is crossed, seeds of a second type can be added to seed pool 520. It is preferable to always have seeds in the seed pool so that planting is maximized. Some seeds of one type can be planted in another region, but the prescription error is minimized. Knowing the number of seeds in seed pool 520 at the fill level sensor 570 and the rate of speed of the tractor, a time delay can be used for the switching of the seed types.

The seed transfer actuators 550 may comprise electric motors. In some single-actuator embodiments, a single seed transfer actuator 550 may drive both seed tenders 560. In one single-actuator embodiment, a single seed transfer actuator 550 has an output shaft which when driven in a first direction drives the first seed tender in a first direction which transfers seed and drives the second seed tender in a second (e.g., opposite) direction which does not transfer seed; thus when the single seed transfer actuator is driven in the first direction, only the first seed tender delivers seed. In another single-actuator embodiment, the single seed transfer actuator drives by both seed tenders 560 means of a clutch (e.g., a sprag clutch) such that when the seed transfer actuator drives an output shaft thereof in a first direction, only the first seed tender is driven, and when the seed transfer actuator drives the output shaft in a second (e.g., opposite) direction, only the second seed tender is driven.

A seed sensor 150 (e.g., an optical or electromagnetic seed sensor configured to generate a signal indicating passage of a seed) is preferably mounted to the seed tube 232 (or the seed conveyor) and disposed to send light or electromagnetic waves across the path of seeds 42. A closing system 236 including one or more closing wheels is pivotally coupled to the row unit 200 and configured to close the trench 38.

Figure 3:
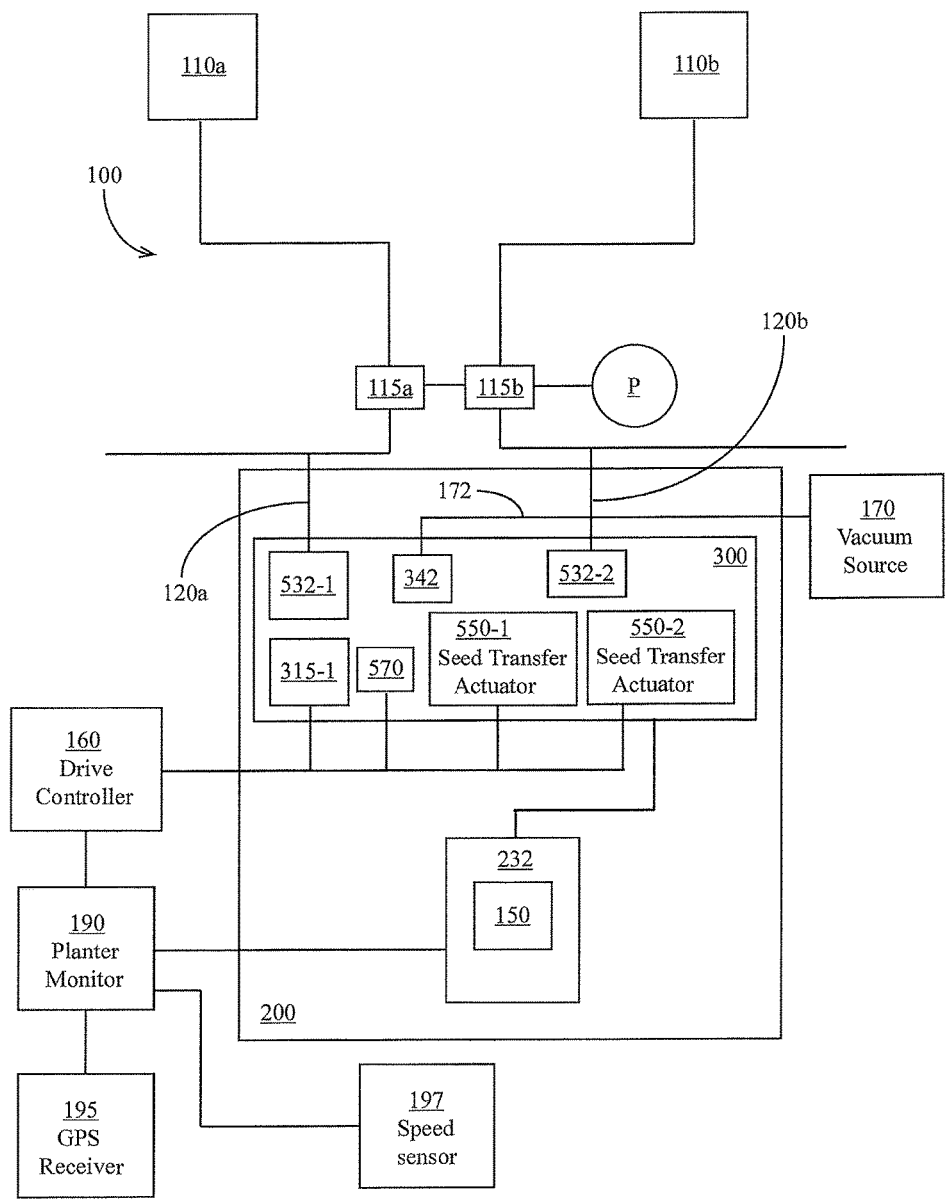
FIG. 3 schematically illustrates an embodiment of a seed variety selection system.

Turning to FIG. 3, a seed variety selection system 100 is illustrated. The system 100 preferably includes a plurality of bulk hoppers 110 (e.g., two bulk hoppers 110a and 110b as illustrated). The first bulk hopper 110a preferably contains a first seed variety (e.g., a first corn seed variety or a first soybean variety); the second bulk hopper 110b preferably contains a second seed variety (e.g., a second corn seed variety or a second soybean variety). Each bulk hopper is preferably in fluid communication with an individual seed entrainer 115. Each seed entrainer 115 is preferably mounted to a lower outlet of the associated bulk hopper 110. Each seed entrainer 115 is preferably in fluid communication with a pneumatic pressure source P and configured to convey air-entrained seeds through a plurality of seed lines 120 to the row units 200. Via a plurality of seed lines 120a, the bulk hopper 110a and the entrainer 115a are preferably in seed communication with a first auxiliary hopper 532-1 of the seed meter 300 of each row unit 200 along the tool bar 14. In operation, the bulk hopper 110a supplies the first seed variety to the first auxiliary hopper 532-1 of the seed meter 300 of each row unit 200. Via a plurality of seed lines 120b, the bulk hopper 110b and the entrainer 115b are preferably in seed communication with a second auxiliary hopper 532-2 of the seed meter 300 of each row unit 200 along the toolbar 14. In operation, the bulk hopper 110b supplies the second seed variety to the second auxiliary hopper 532-2 of the seed meter 300 of each row unit 200.

Continuing to refer to FIG. 3, the drive 315 is preferably in data communication with a drive controller 160. The drive controller is preferably configured to generate a drive command signal corresponding to a desired rate of seed disc rotation. The drive controller 160 is preferably in data communication with a planter monitor 190. The planter monitor 190 preferably includes a memory, a processor, and a user interface. The planter monitor is preferably configured to send drive command signals and/or desired rates of seed disc rotation to the drive controller 160. The planter monitor 190 is preferably in data communication with a GPS receiver 195 mounted to either the planter 10 or the tractor used to draw the planter. The planter monitor 190 is preferably in data communication with a speed sensor 197 (e.g., a radar speed sensor) mounted to either the planter 10 or the tractor. As used herein, "data communication" may refer to any of electrical communication, electronic communication, wireless (e.g., radio) communication, or communication by any other medium configured to transmit analog signals or digital data.

Continuing to refer to FIG. 3, each vacuum port 342 is preferably in fluid communication with a vacuum source 170 via a vacuum line 172.

Continuing to refer to FIG. 3, the seed meter 300 of the row unit 200 is preferably in seed communication with (e.g., disposed to deposit seed into) a seed tube 232 (or seed conveyor) associated with the row unit 200. The seed sensor 150 associated with the seed tube 232 of each row unit 200 is preferably in data communication with the planter monitor 190.

Continuing to refer to FIG. 3, the planter monitor 190 is preferably in data communication with a fill level sensor 570 associated with the meter 300 and one or more seed transfer actuators 550 associated with the meter 300.

Figure 9:
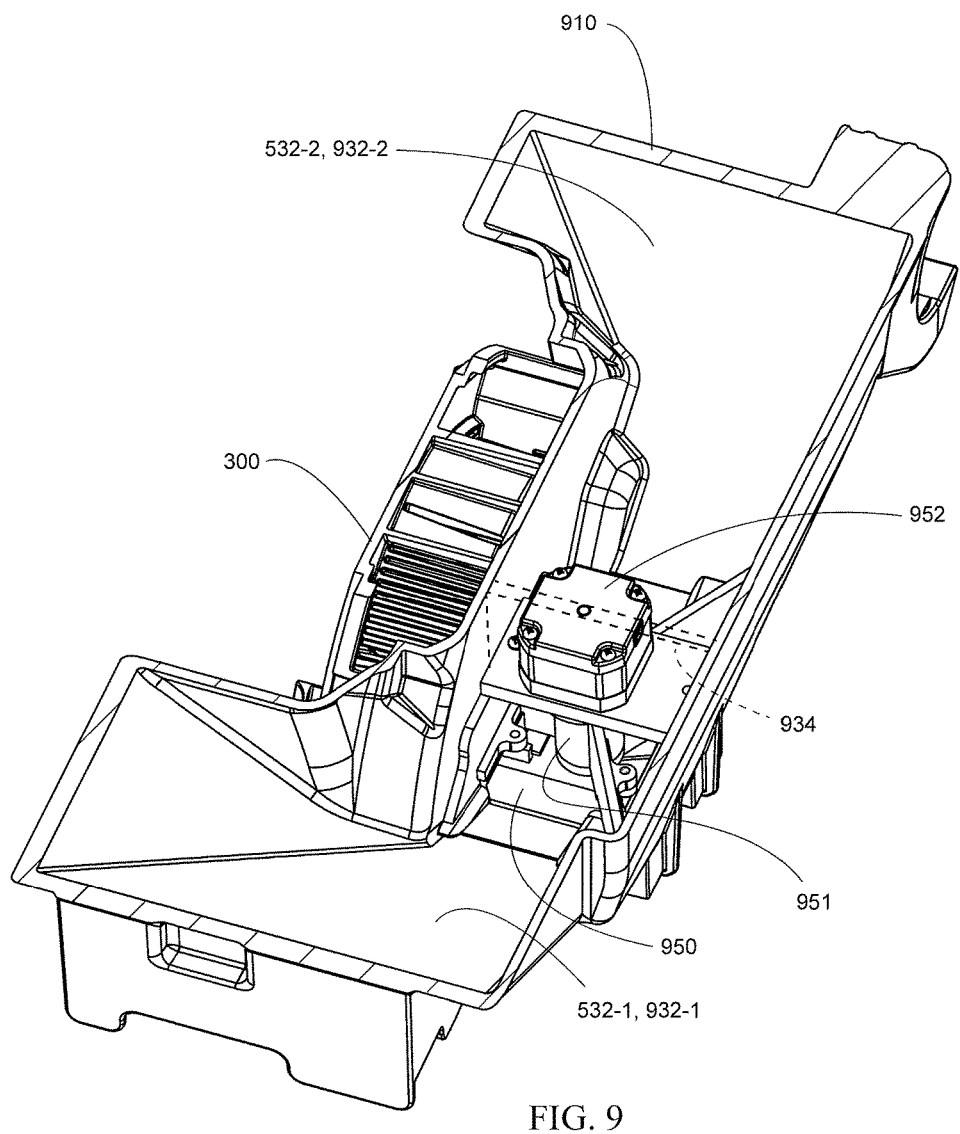
FIG. 9 is another embodiment for selectively supplying seed to a seed meter showing a partial cut-away perspective view of row unit seed hopper divided into compartments and utilizing seed transfer actuator in the form of a rotating gate.
Figure 10:
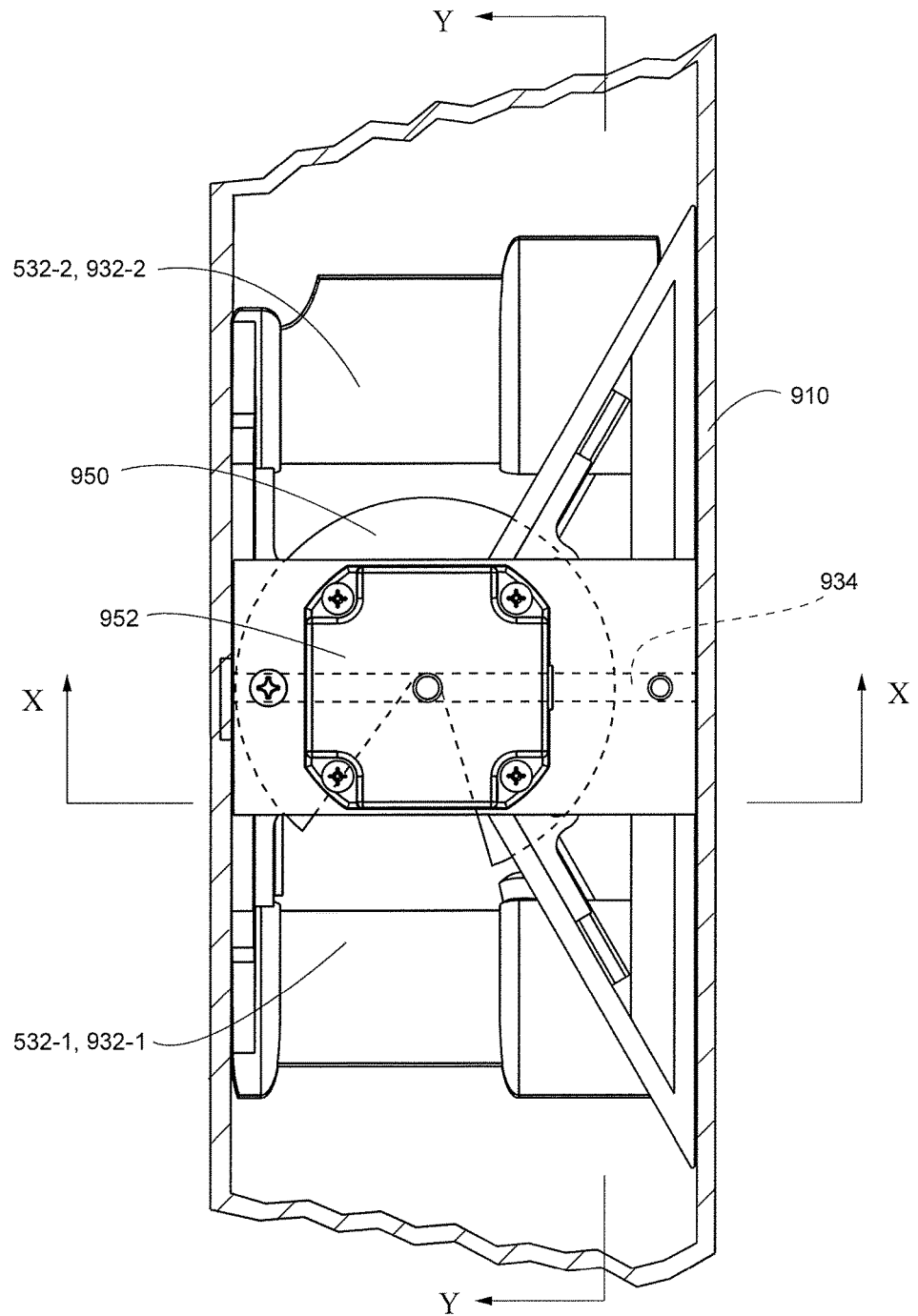
FIG. 10 is a top plan view of the embodiment of FIG. 9 showing the rotating gate.
Figure 12:
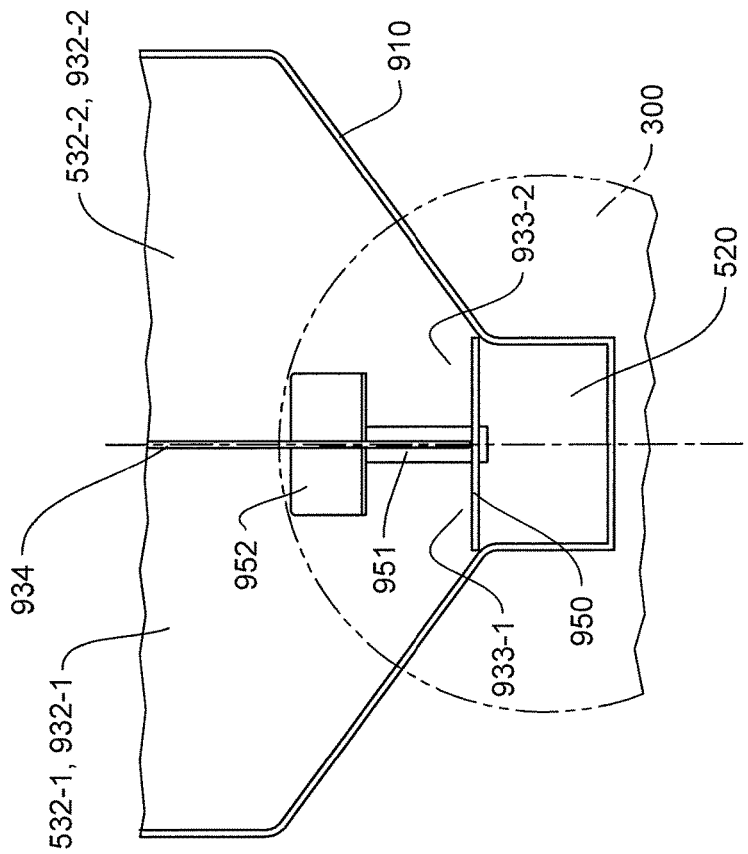
FIG. 12 is a cross-sectional view along lines Y-Y of FIG. 10.
Figure 11:
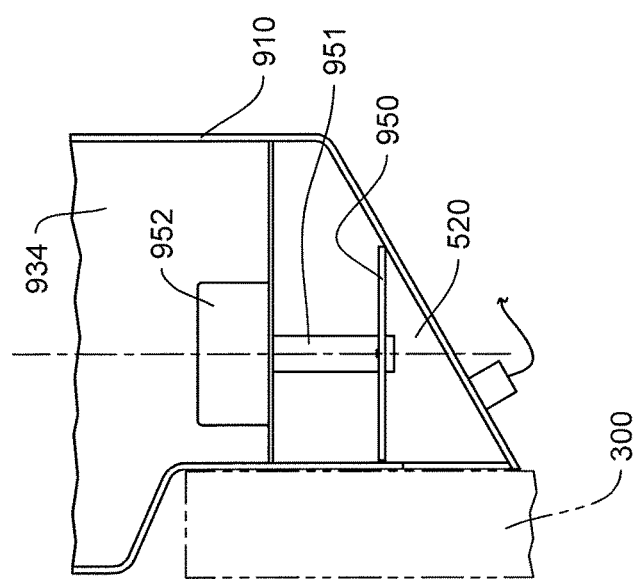
FIG. 11 is a cross-sectional view along lines X-X of FIG. 10.

FIGS. 9-13 illustrate another embodiment for selectively supplying seed to a seed meter 300 wherein the first auxiliary hopper 532-1 and the second auxiliary hopper 532-2 are separate compartments 932 within a row unit seed hopper 910. FIG. 9 is a top perspective view showing a partial cutaway of the hopper 910. FIG. 10 is a partial top plan view. FIG. 11 is a cross-sectional view as viewed along lines x-x of FIG. 10. FIG. 12 is a cross-sectional view as viewed along lines Y-Y of FIG. 10. It should be appreciated that the hopper 910 may be divided into a plurality of compartments 932 each holding a different seed variety. The row unit seed hopper 910 is shown with first compartment 932-1 and second compartment 932-2, separated by a divider panel 934. First compartment 932-1 has a first seed passage 933-1, and second compartment 932-2 has a second seed passage 933-2, both of which are in communication with seed transfer actuator 950. Seed transfer actuator 950 is disposed in the bottom of row unit seed hopper 910 to allow for gravity feed of the seed through the first seed passage 933-1 and second seed passage 933-2. Seed transfer actuator is in communication with the seed pool 520 and is rotated by a shaft 951 and motor 952.

Figure 13:
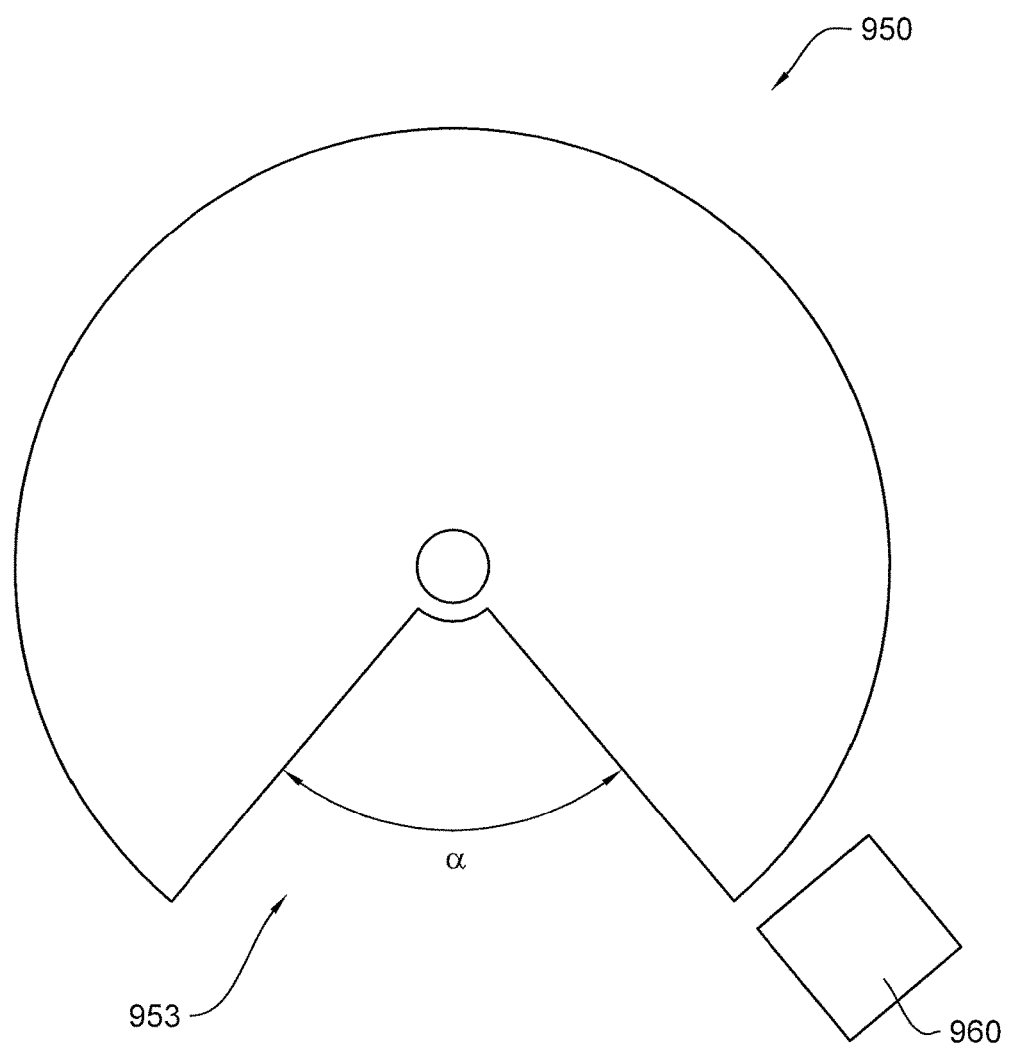
FIG. 13 is a top plan view of the rotating gate of FIG. 10.

Seed transfer actuator 950 is shown in greater detail in FIGS. 10 and 13. In this embodiment, seed transfer actuator 950 is a rotating gate that rotates about a vertical axis A-A. There is an opening 953 in seed transfer actuator 950 which is rotated to align with the seed passage 933 thereby allowing the seeds to pass from the respective compartment 932 to pass through the passage 933 and the opening 953 into the seed pool 520 below. The angle a creating the opening can be any angle that permits one compartment 932 or no compartments 932 to be in communication with seed pool 520. It will be appreciated that with an increasing number of compartments, the angle a will decrease. For the two compartment embodiment shown, angle a is less than 120°. In another embodiment, angle a is less than 90° or about 80°. This rotating gate configuration is simpler to operate compared to a drop gate or a rotary gate rotating about a horizontal axis in that gravity can be used as the driving force to move the seed.

Figure 14:
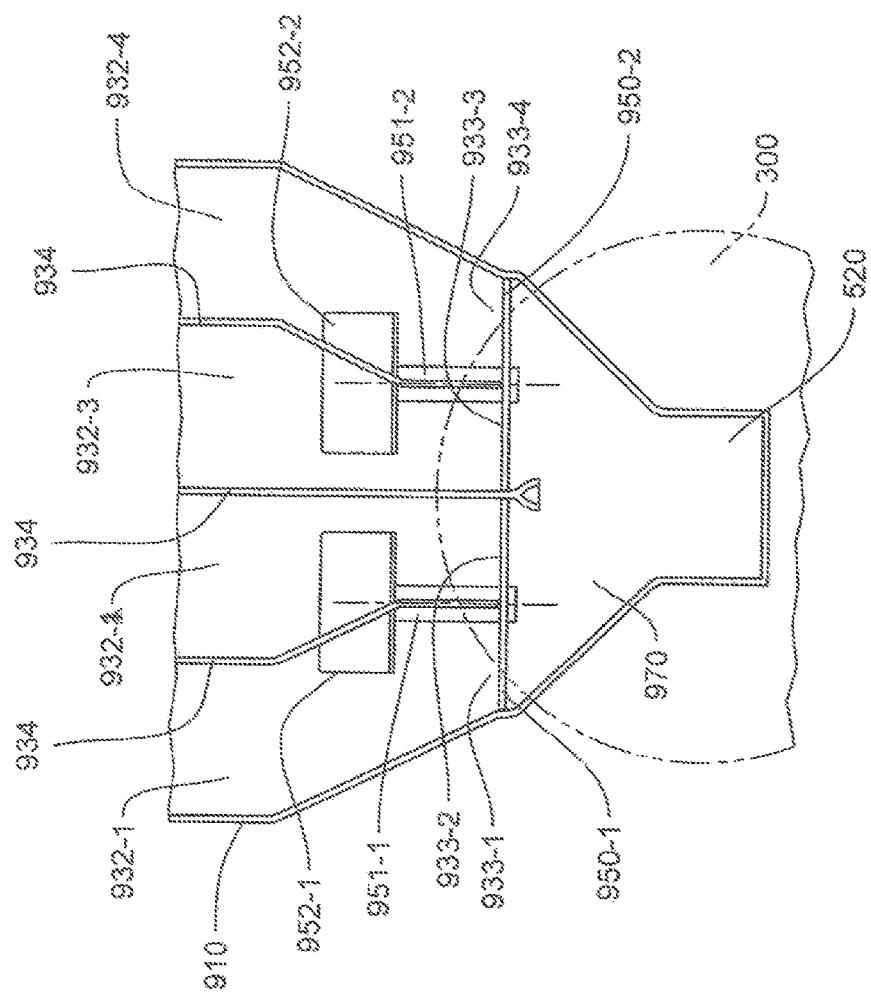
FIG. 14 is a cross-sectional view of an embodiment of a row unit seed hopper similar to FIG. 12 but four compartments and showing an embodiment of a seed pool feeder.

It should be appreciated that as the number of compartments increase, the openings 953 may become so small that seed flow may be too slow to feed the seed pool 520. As shown in FIG. 14, a seed hopper 910 may be divided into four compartments 932-1, 932-2, 932-3, 932-4 with a seed pool feeder 970 disposed below the compartments which is in communication with the seed pool 950 of the seed meter 300. In this embodiment, a first seed transfer actuator 950-1 is disposed to be in communication with a first compartment 932-1 and a second compartment 932-2, and a second seed transfer actuator 950-2 is disposed to be in communication with third compartment 932-3 and fourth compartment 932-4. In operation, one of the seed transfer actuators 950-1 or 950-2 can be commanded to open to allow seeds to flow through one of the respective seed passages 933-1, 933-2, 933-3, 933-4 and into seed pool feeder 970.

The seed transfer actuator 950 can further include a Hall effect sensor 960 to set a home position of the rotating gate and determining the rotation of seed transfer actuator 950 about the vertical axis.

A benefit of the system is a simplification of each row unit in that only one seed meter is needed at each row unit to plant multiple types of seeds. This reduces the number parts and the cost.

Figure 6:
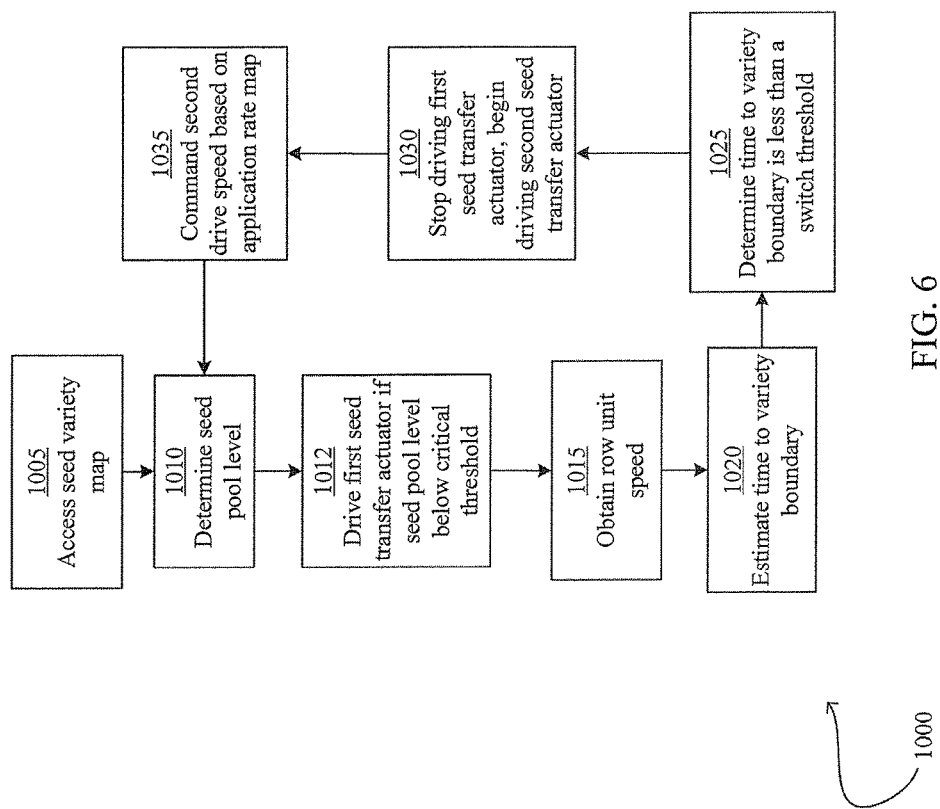
FIG. 6 illustrates an embodiment of a process for changing seed varieties.

Turning to FIG. 6, a process 1000 is illustrated for selecting a seed variety planted by the row units 200 of the variety selection system 100. At step 1005, the planter monitor 190 preferably accesses a seed variety map, preferably stored in the memory of the planter monitor. The seed variety map preferably comprises a file (e.g., a shape file) associating desired seed types with geo-referenced locations. In other embodiments, two separate maps may be used to independently control the seed transfer actuators; in such embodiments the a first map preferably instructs the first seed transfer actuator not to transfer seeds at locations for which the second map instructs the second meter to transfer seeds, and vice versa.

At step 1010, the planter monitor 190 preferably repeatedly determines a seed pool level (e.g., an amount of seeds, height of seeds, or number of seeds) in the seed pool of a first variety stored in auxiliary hopper 532-1. For example, the planter monitor 190 may determine the seed pool level based on the signal from the fill level sensor 570. Alternatively or additionally, the planter monitor 190 may determine the seed pool level based on an estimated amount of seed transferred by the seed tenders 560-1 (e.g., based on a number of rotations of an output shaft of the seed transfer actuator 550) during a preceding time period and/or a number of seeds planted (e.g., based on seed sensor pulses or measured or commanded seed disc rotations) during the same time period.

At step 1010, if the planter monitor 190 determines the seed pool level is below a critical threshold (e.g., a level required for operation of the seed meter), the planter monitor 190 preferably commands the seed tender 560 to transfer seeds to the seed pool 520 (e.g., until the seed pool level again meets the critical threshold).

At step 1015, the planter monitor 190 preferably obtains the speed of the row unit 200 using one of the methods disclosed in the '327 application. At step 1020, the planter monitor 190 preferably estimates the time to the nearest variety boundary, e.g., by dividing the distance to the variety boundary by the speed of the row unit.

At step 1025, the planter monitor 190 preferably determines that the time to the variety boundary is less than a switch threshold. The switch threshold may correspond to the time required to fill the seed pool to the critical threshold.

At step 1030, upon making the determination of step 1025, the planter monitor 190 preferably stops driving the first seed transfer actuator 550-1. The planter monitor 190 may then optionally wait for seed to be planted from the seed pool 520 until determining that the critical threshold (or another fill threshold such as a higher or lower fill threshold) has been reached as seeds of the first variety are planted from the seed pool 520. The planter monitor 190 then preferably begins driving the second seed transfer actuator 550-2 in order to transfer seeds of the second variety from the auxiliary hopper 532-2 to the seed pool 520.

At step 1035, the planter monitor preferably commands a speed to the second drive 315-2 based on an application rate map stored in the memory of the planter monitor and associating desired application rates with georeferenced locations.

Figure 8:
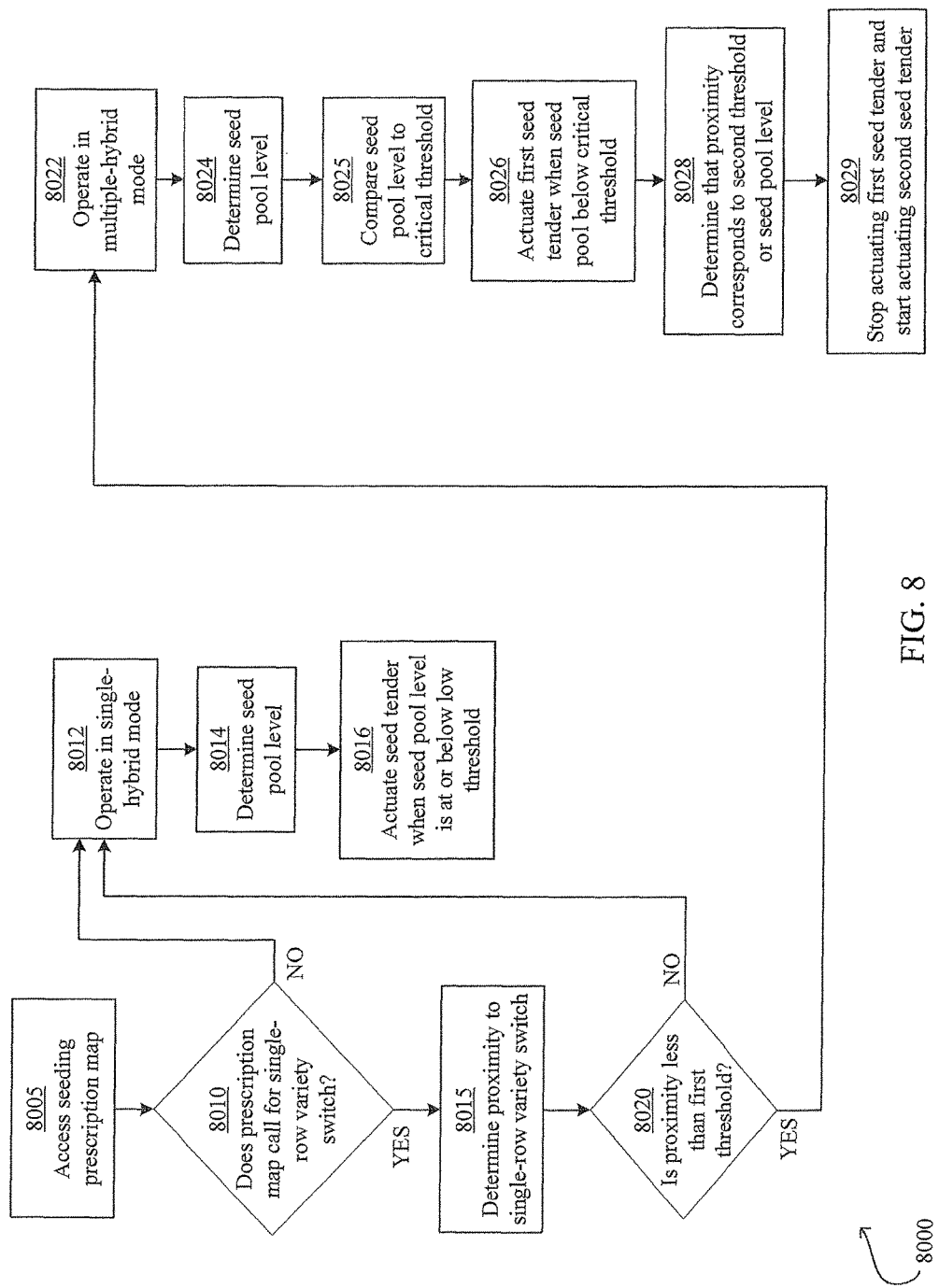
FIG. 8 illustrates another embodiment of a process for changing seed varieties.

Turning to FIG. 8, a process 8000 is illustrated for selecting a seed variety planted by the row units 200 of the variety selection system 100. At step 8005, the planter monitor 190 preferably accesses a seeding prescription map, e.g., a map associating geo-referenced positions in the field with desired seeding rates and/or desired seed varieties.

At step 8010, the planter monitor 190 preferably determines whether the prescription map calls for a single-row variety switch, e.g., whether a row unit 200 should alternate seed types during planting in order to implement the prescription. The determination of step 8010 may be made (1) based on a user input; (2) by determining whether the prescription map calls for planting more than one seed variety in the field; or (3) by determining whether a predicted or desired planting plan includes a single row unit pass that crosses over sub-regions of the field for which the prescription calls for two or more seed varieties.

If the result of step 8010 is "No", then at step 8012 the planter monitor 190 preferably begins to operate in a single-hybrid mode described in more detail below. If the result of step 8010 is "Yes", then upon beginning the planting operation, at step 8015 the planter monitor 190 preferably repeatedly (e.g., at regular intervals such as every 10 seconds or every 10 feet of travel of the implement) determines a proximity of each row unit 200 to a single-row variety switch.

The proximity determination of step 8015 may be made based on the shortest distance between the contemporaneous (e.g., GPS-reported) position of the implement (e.g., the row unit 200 of the planter) and any boundary between seed variety regions along the current travel direction of the implement. The proximity may be determined in terms of any of the following: (1) distance (e.g., simply the shortest distance described in this paragraph); time (e.g., the estimated time required to travel the shortest distance based on the contemporaneous radar- or GPS-reported implement speed); or number of seeds (e.g., a number of seeds to be planted along the shortest distance based on the planting rate or population called for by the seeding prescription).

At step 8020, the planter monitor 190 preferably compares the proximity determined at step 8015 to a first proximity threshold (e.g., a threshold distance, time, or number of seeds depending on the type of proximity determined at step 8015) and determines whether the proximity is less than the proximity threshold.

If the result of step 8020 is "No", then at step 8012 the planter monitor 190 preferably begins to operate in a single-hybrid mode (described in more detail below) until the result of step 8020 is "Yes". If the result of step 8020 is "Yes", then at step 8022 the planter monitor 190 preferably begins to operate in a multiple-hybrid mode (described in more detail below).

One embodiment of a single-hybrid mode begun at step 8012 comprises the following steps. At step 8014, the planter monitor 190 preferably determines a seed pool level according to one of the methods described herein with respect to process 1000. At step 8014, the planter monitor 190 preferably actuates a first seed tender (e.g., drives a seed transfer actuator such that a the first seed tender such as a first auger transfers seed from a first seed hopper to the seed pool) upon determining that the seed pool is below a "low" threshold such as that described herein with respect to process 1000.

One embodiment of a multiple-hybrid mode begun at step 8022 comprises the following steps. At step 8024, the planter monitor 190 preferably determines a seed pool level according to one of the methods described herein with respect to process 1000. At step 8025, the planter monitor 190 preferably compares the seed pool level to a "critical" threshold such as that described herein with respect to process 1000. The "critical" threshold preferably corresponds to a lower threshold (e.g., lower seed pool height, smaller number of seeds) than the "low" threshold. The "critical" threshold may correspond to a number of seeds between 10 and 100 seeds for corn seed, e.g., 10, 20, 30, 40, 50, 60, 70, 80, or 90 seeds. In some embodiments, the "critical" threshold may be determined by referencing a database relating one of a plurality of "critical" thresholds to various combinations of crop types, seeding rates, and implement speeds. At step 8026, upon determining that the seed pool is below the "critical" threshold, the planter monitor 190 preferably actuates the first seed tender. At step 8028, the planter monitor 190 preferably determines that the proximity to a variety switch (e.g., to a variety switch boundary) corresponds to a second proximity threshold. The second proximity threshold is preferably lower than the first proximity threshold. In other embodiments, at step 8028 the planter monitor 190 instead determines that the proximity to a variety switch corresponds to the seed pool level; for example, by determining that a proximity value measured in seeds (or corresponding to a number of seeds) corresponds to the number of seeds to be planted. Once the determination of step 8028 has been made, the planter monitor 190 optionally delays step 8029 until an optional delay (e.g., a threshold time, a threshold distance traveled, a threshold number of seeds planted and detected by the seed sensor 150) has passed. At step 8029, the planter monitor 190 preferably stops actuating the first seed tender and begins actuating the second seed tender. After step 8029, the planter monitor 190 preferably returns to step 8015 to determine the proximity to the next variety switch.

In another embodiment, the seed variety system 100 can measure the size of seeds. This eliminates having to know the size of seeds to approximate the number of seeds in seed pool 520. Seed sensor 150 and fill level sensor 570 are used in conjunction. This combination will be illustrated with the embodiment described in FIGS. 9-13.

Figure 15:
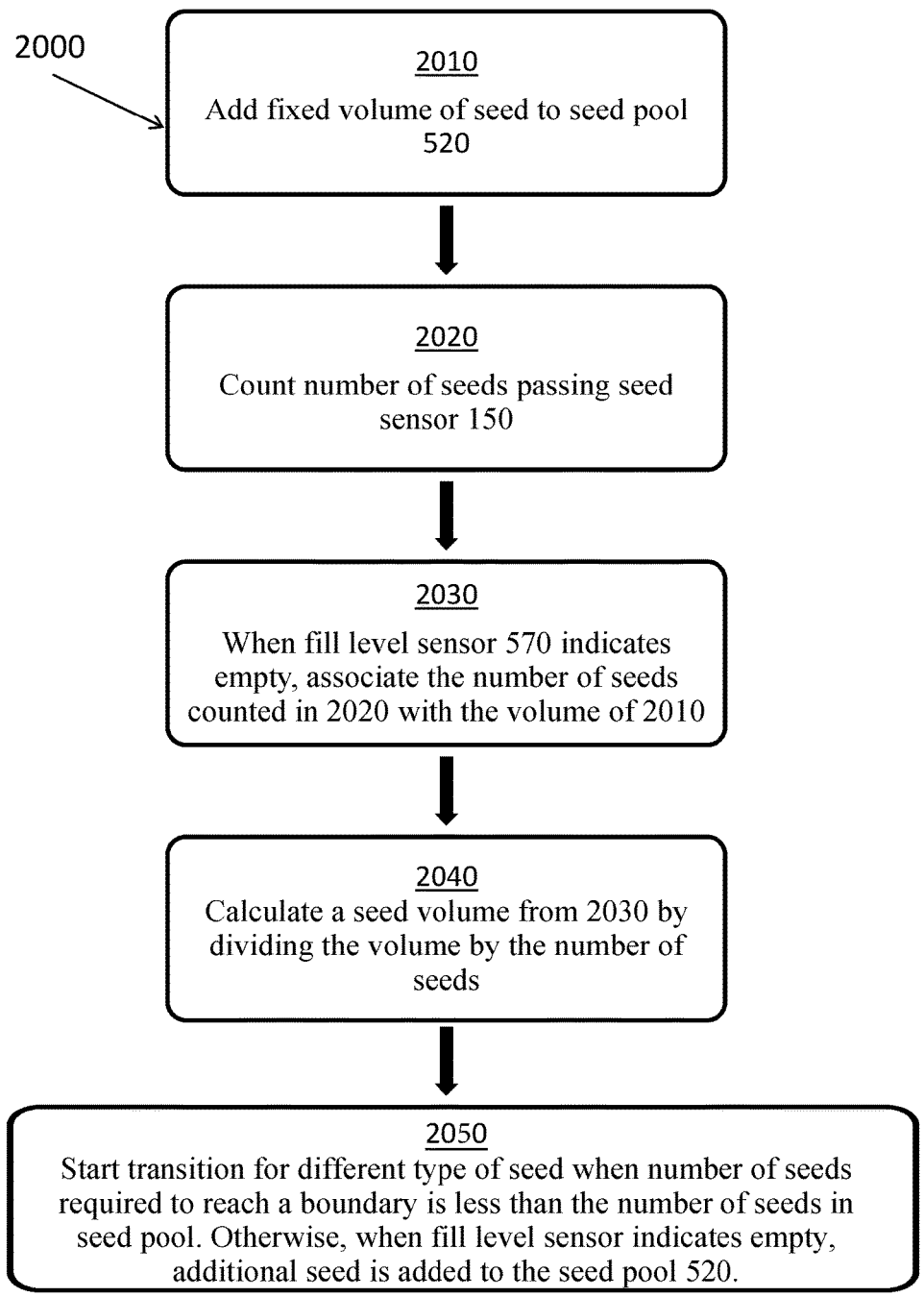
FIG. 15 illustrates a method for determining seed volume in accordance with one embodiment.

Fill level sensor 570 is disposed in seed pool 520 such that a volume in seed pool 520 below the fill level sensor is known. Seed sensor 150 counts the number of seeds passing the seed sensor. When fill level sensor 570 detects that the level of seeds in seed pool 520 is below fill level sensor 570, a signal is sent to actuator 950 to provide an opening to the selected compartment (932-1 or 932-2) in hopper 910 for a set period of time to allow a set volume of seed to be dumped into seed pool 520. After each dump, the number of seeds passing seed sensor 150 is counted until the next dump. The number of seeds counted along with the volume of seeds dumped is used to calculate seed volume by dividing the volume by the number of seeds as illustrated in a method 2000 of FIG. 15 in accordance with one embodiment. The method 2000 is performed by processing logic that may comprise hardware (circuitry, dedicated logic, etc.), software (such as is run on a general purpose computer system or a dedicated machine or a device), or a combination of both. In one embodiment, the method 2000 is performed by components (e.g., a planter monitor 190, a processor, a fill level sensor 570 associated with the meter 300, seed transfer actuators 550 associated with the meter 300, seed pool 520) of the seed varietal selection system 100.

At operation 2010, a fixed volume of seed is added to a seed pool (e.g., seed pool 520). At operation 2020, a number of seeds passing a seed sensor (e.g., seed sensor 150) is counted. A number of gate openings can also be counted to calculate a running average and then calculate the number of seeds per gate opening. The number of seeds per gate opening can be correlated to seed size. The running average can be used for each seeds per dump calculation to have an ongoing average seed size. It will be appreciated that in a given volume there are fewer larger seeds as compared to smaller seeds. For example, when planting large seed, fewer seeds are dispersed per gate opening than small seeds.

At operation 2030, when a fill level sensor 570 indicates empty, the number of seeds counted at operation 2020 is associated with the volume of seed added at operation 2010. At operation 2040, a seed volume is calculated based on the volume of seed added and the number of seeds counted. For example, the seed volume can be calculated by dividing the volume of seed added by the number of seeds counted. Once the seed volume (e.g., seed size) is determined, then the number of seeds still in the seed meter will be known with the number of seeds being based on the sensitivity of the seed pool level sensor.

As described above, knowing the seed size and the number of seeds in the seed pool 520 allows for transitions between seed types as a boundary is approached to minimize blending of seeds across a boundary.

When the number of seeds required to reach a boundary is less than the number of seeds in seed pool 520, then a transition mode is started at operation 2050. Otherwise, when fill level sensor 570 indicates empty, additional seed is added to seed pool 520.

In the following example, there are 100 seeds in seed pool 520 when fill level sensor 570 indicates empty. For a transition between hybrids, a number of seeds passing seed sensor 150 is counted. When a number of seeds (e.g., 60 seeds pass seed sensor 150) in the seed pool reach a preset transition (e.g., 40 seeds), then there are approximately 40 seeds remaining in seed pool 520. At this point, actuator 950 is actuated to open the other compartment 932-2 or 932-1 to seed pool 520 to add the other variety of seed to seed pool 520. The selection of the number of seeds to remain in seed pool 520 is based on having a sufficient number of seeds to avoid having seed pool 520 be totally empty to avoid missed planting and minimizing the transition time between seed types.

The above process can be used with each seed type to calculate the size of each seed type. Calculations for a first seed type before switching to a second seed type can be used again when switching back to the first seed type.

What is claimed is:

1. A method of calculating a volume of a seed during planting comprising:
   adding a known volume of seed to a seed pool, wherein the seed pool has a fill level sensor;
   dispensing seeds from the seed pool, and as the seeds are dispensed, counting the number of seeds with a seed sensor;
   stopping counting when the fill level sensor indicates a seed level in the seed pool is below a fill level; and
   calculating seed volume based on the known volume and the number of seeds counted.

2. The method of claim 1, further comprising:
   detecting with the fill level sensor that the seed level in the seed pool is below the fill level;
   sending a signal to an actuator to provide a gate opening within a hopper for a set period of time to allow a set volume of seed to be filled into the seed pool in response to the fill level sensor detecting that the seed level in the seed pool is below the fill level.

3. The method of claim 2, further comprising:
   determining a number of gate openings within the hopper to calculate a running average of seeds per gate opening during dispensing of the seeds; and
   correlating the running average of seeds per gate opening with seed size.

4. The method of claim 3, further comprising:
   using the running average per fill calculation to determine an average seed size.

5. The method of claim 1, wherein the seed volume including a seed size is calculated by dividing the known volume of seed added by the number of seeds counted.

6. The method of claim 5, further comprising:
   determining the number of seeds currently in the seed pool based on calculating the seed size.

7. The method of claim 6, wherein the number of seeds currently in the seed pool is based on the sensitivity of the fill level sensor.

8. The method of claim 6, further comprising:
   starting a transition mode for a different type of seed when the number of seeds required to reach a boundary is less than the number of seeds in the seed pool.

9. The method of claim 6, further comprising:
   determining when a number of seeds in the seed pool reach a preset transition.

10. The method of claim 9, further comprising:
    actuating an actuator to open a gate opening within the hopper to add a different seed type to the seed pool when the number of seeds in the seed pool reach the preset transition.

11. A method comprising:
    adding a known volume of a first variety of seed to a seed pool of a seed variety system, wherein the seed pool has a fill level sensor;
    dispensing seeds from the seed pool;
    counting the number of seeds with a seed sensor of the seed variety system during the dispensing until the fill level sensor indicates a seed level in the seed pool is below a predetermined fill level; and
    calculating seed volume based on the known volume and the number of seeds counted for the first variety of seed.

12. The method of claim 11, further comprising:
    detecting with the fill level sensor that the seed level in the seed pool is below the predetermined fill level; and
    sending a signal to a first actuator to provide a gate opening within a hopper of the seed variety system for a set period of time to allow a set volume of the first variety of seed to be filled into the seed pool in response to the fill level sensor detecting that the seed level in the seed pool is below the fill level.

13. The method of claim 12, further comprising:
    determining a number of gate openings within the hopper to calculate a running average of seeds per gate opening during dispensing of the first variety of seed; and
    correlating the running average of seeds per gate opening with seed size for the first variety of seed.

14. The method of claim 13, further comprising:
    using the running average per fill calculation to determine an average seed size for the first variety of seed.

15. The method of claim 11, wherein the seed volume including a seed size for the first variety of seed is calculated by dividing the known volume of seed added by the number of seeds counted for the first variety of seed.

16. The method of claim 15, further comprising:
    starting a first transition mode for a second variety of seed when the number of seeds of the second variety of seed required to reach a boundary is less than the number of seeds in the seed pool for the first variety of seed; and
    actuating a second actuator to open a gate opening within the hopper to add the second variety of seed to the seed pool during the transition mode or upon completing the transition mode.

17. The method of claim 16, further comprising:
    starting a second transition mode for the first variety of seed when the number of seeds of the second variety of seed required to reach a boundary is less than the number of seeds of the second variety of seed in the seed pool; and
    actuating the first actuator to open a gate opening within the hopper to add the first variety of seed to the seed pool during the second transition mode or upon completing the second transition mode.

18. A seed variety system, comprising:
    a seed pool for dispensing seed during planting operations;
    a fill level sensor to indicate a seed level in the seed pool; and
    processing logic to perform operations including adding a known volume of a first type of seed to the seed pool, dispensing seeds from the seed pool, counting the number of seeds with a seed sensor during the dispensing until the fill level sensor indicates a seed level in the seed pool is below a fill level, and calculating seed volume based on the known volume and the number of seeds counted for the first type of seed.

19. The seed variety system of claim 18, wherein the processing logic to perform operations further including sending a signal to a first actuator to provide a gate opening within a hopper of the seed variety system for a set period of time to allow a set volume of the first type of seed to be filled into the seed pool in response to the fill level sensor detecting that the seed level in the seed pool is below the fill level.

20. The seed variety system of claim 19, wherein the processing logic to perform operations further including starting a transition mode for a second type of seed when the number of seeds of the first type of seed required to reach a boundary is less than the number of seeds in the seed pool and actuating a second actuator to open a gate opening within the hopper to add the second type of seed to the seed pool during the transition mode or upon completing the transition mode.

* * * * *